United States Patent
Menhardt et al.

(10) Patent No.: US 7,494,045 B2
(45) Date of Patent: Feb. 24, 2009

(54) PATIENT IDENTIFICATION METHOD FOR X-RAY FILM USER-INTERFACES

(75) Inventors: Wido Menhardt, Los Gatos, CA (US); Yue Shen, Santa Clara, CA (US)

(73) Assignee: Carestream Health, Inc., Rochester, NY (US)

( * ) Notice: Subject to any disclaimer, the term of this patent is extended or adjusted under 35 U.S.C. 154(b) by 647 days.

(21) Appl. No.: 10/526,328

(22) PCT Filed: Sep. 4, 2003

(86) PCT No.: PCT/CA03/01285

§ 371 (c)(1),
(2), (4) Date: Feb. 28, 2005

(87) PCT Pub. No.: WO2004/023790

PCT Pub. Date: Mar. 18, 2004

(65) Prior Publication Data

US 2006/0000884 A1    Jan. 5, 2006

Related U.S. Application Data

(60) Provisional application No. 60/408,079, filed on Sep. 4, 2002.

(51) Int. Cl.
*G06F 17/00* (2006.01)
*G06K 19/00* (2006.01)

(52) U.S. Cl. .................. 235/375; 235/487
(58) Field of Classification Search ............ 235/375, 235/380, 487; 382/132
See application file for complete search history.

(56) References Cited

U.S. PATENT DOCUMENTS

| | | | |
|---|---|---|---|
| 5,418,355 A | 5/1995 | Weil | |
| 5,680,223 A | 10/1997 | Cooper et al. | |
| 6,198,837 B1 * | 3/2001 | Sasano et al. | 382/132 |
| 6,556,698 B1 * | 4/2003 | Diano et al. | 382/132 |

FOREIGN PATENT DOCUMENTS

| | | |
|---|---|---|
| EP | 0952726 | 10/1999 |
| JP | 10-057363 | 3/1998 |
| WO | 02/098214 | 2/2002 |

\* cited by examiner

*Primary Examiner*—Thien M. Le
*Assistant Examiner*—April A Taylor (57) ABSTRACT

A method and system for identifying a digitized x-ray film having at least one label. The method includes the steps of: obtaining a digital image of said label; digitally associating said digitized image of the label with said digitized x-ray film; and displaying said digital image of said label thereby allowing a user to identify said digitized x-ray film.

17 Claims, 6 Drawing Sheets

| LABEL ID | ENHANCED LABEL ID | CAD RESULT |
|---|---|---|
| ⋮ | ⋮ | ⋮ |
| L 3 | EL 3 | CAD 3 |
| ⋮ | ⋮ | ⋮ |

Selection of Label
( or Enhanced Label)

PATIENT IDENTIFICATION METHOD FOR X-RAY FILM USER-INTERFACES

CROSS-REFERENCE TO RELATED APPLICATIONS

This application claims priority on Application No. PCT/CA2003/001285 filed on Sep. 4, 2003 and published as WO 2004/023790, which claims priority from U. S. provisional application Ser. No. 60/408,079, filed Sep. 4, 2002 entitled "Patient identification method for CAD user-interfaces".

TECHNICAL FIELD

This invention relates to the field of X-ray film identification and more particularly to identification of digitized X-ray films in computer user interfaces.

BACKGROUND OF THE INVENTION

X-ray films can be scanned by a film digitizer, and converted into digital format. Digitized films can then be stored for future retrieval or analyzed with image analysis algorithms such as Computer Aided Detection (CAD). Film digitizers are available from, for example, Canon, Howtek, Kodak, or Vidar. The film digitizer is, connected to a standard computer and a standard user interface controls scanning, identifying, and storing the digitized films as images on disk. Standard user interfaces for digitizer control, including quality control, error detection, and error recovery, are available from Vidar, Applicare, or Merge.

In the diagnosis process, quick and reliable identification of the film is required to increase the efficiency of the process and reduce the risk of errors associated with misidentification. Furthermore digitized X-ray films are often analyzed with software applications such as CAD and reliable association of the CAD results with the corresponding digitized X-ray film is very important.

In a typical scenario, the radiologist normally reads the film mammograms on an alternator or on a light box. Suspicious findings are noted by the radiologist, and recorded in a medical report. However, a non-zero percentage of cancers are typically missed by radiologists. To decrease the rate of false negative, a second radiologist may read the films, and the results of both radiologists are compared.

The results of CAD can be used in much the same way as a second radiologist. In one scenario, also referred to as "second read with CAD", the radiologist first reads the films without the aid of a computer. Once the radiologist has noted her findings, she reviews the suspicious areas identified by CAD analysis, for example on a monitor as an overlay over the digitized versions of the mammogram, or printed on paper. The suspicious areas may confirm the findings of the radiologist. Or, the radiologist may be prompted to re-examine areas she had not found to be suspicious, but which were highlighted by the computer.

In another scenario, also referred as "cued read with CAD", the radiologist may read the films and review the CAD results at the same time, moving back and forth between them using the CAD results to "cue" her reading.

In either scenario, it is important to ensure that the CAD results are properly associated with the X-ray films to ensure correct identification of the results and avoid "mix-up" of the films and CAD results. Commercial products currently use a number of methods for to achieve this.

For example a bar code system can be used. When films are digitized, a separator sheet of the same approximate size of the films is also scanned. It serves as a separator between the films of one case and the films of the next case. A bar code is printed on the separator sheet. The digitization system reads the bar code, and digitally associates it with the images. The operator enters no patient name, accession number, or other identifier, the bar code information is the identifier of the case only the numerical identifier corresponding to the bar code (a number) identifies the patient. After the digitization, the films are replaced in the jacket, together with the separator sheet with the bar code.

When the films are hung on the alternator, a bar code reader is used to scan the bar code on separator sheets. The alternator contains a computer and logic to associate the CAD results with a particular alternator position (that of the corresponding X-ray films). That way, the proper digital images and CAD results are displayed on the mini-monitors integrated into the alternator depending on the alternator position. The numerical identifier corresponding to the bar code (together with the alternator position) identities the patient.

This method is deficient in that radiologists and other medical personnel use patient names and patient record identifiers to identify patients, and cross-correlate patients to other medical information, reports, requisitions, and the like. Since the CAD results are identified only with a barcode and its associated numerical identifier, association of patient names or records with CAD results involves an indirect and unreliable cross-referencing method from CAD results to bar code to patient name. This method is not only inconvenient and time consuming, but also prone to errors.

In other systems a bar code sticker is affixed to each individual film (the sticker includes the orientation information of each individual film). The digitizer uses the bar code to associate it with the films of the patient. When the films are reviewed, a bar code reader is used to read the bar code stickers on the films, and the appropriate images are displayed on a monitor, together with the CAD results. In this system the CAD results are not associated with alternator positions. This method is equally deficient in that the only mechanism to correlate CAD results with a patient name is to cross-correlate the bar code numbers of the CAD results with a bar code label affixed to an X-ray film.

Yet another method is, described in "Hybrid display for simultaneous side-by-side review of radiographs", U.S. Pat. No. 5,748,173. In the described system, patient information in the form of a name or a patient number is obtained directly from the film that is placed on a view box (alternator or light box) using a bar code scanner or a CCD camera. This method is also deficient in that the CAD results have to be identified by other means with the patient name or patient number before they can be recalled with the method described here.

Other strategies have also been used to identify X-ray films. For example the operator can enter the patient name and identification. The patient name is then digitally associated with the digitized images. When a case is reviewed, the radiologist enters the patient name in a computer, and the appropriate images and CAD results are displayed. Alternatively, the radiologist can select the patient name from a list. A disadvantage of this method is that the patient name has to be entered manually at the time of digitization, and potentially again at the time of review.

SUMMARY OF THE INVENTION

In one aspect of the present invention there is provided a method whereby human-readable patient information on a label is automatically obtained from digitized X-ray film.

This human-readable patient information is then used to identify the corresponding X-ray film. In one aspect of the invention the label of a digitized X-ray film is digitally extracted and associated with the corresponding film and displayed such as to be readable by a user. This advantageously avoids the need to identify the film by indirect means such as by scanning a bar code affixed to the film or by having to enter the name or identification number of a patient and therefore overcomes several disadvantages of the prior art.

In one embodiment of the invention the digitally extracted label can be enhanced to increase the contrast or to remove textured background to facilitate reading by the user of the alpha-numeric information contained in the label.

The digitized label may also be associated with results of X-ray film image analysis such as Computer Aided Detection Analysis (CAD). The human-readable label may be used in user-interfaces related to CAD, including but not limited to, quality control of digitized X-ray films, worklist preparation for review of X-ray films with CAD, selection of CAD results for the purposes of review of X-ray films, display of CAD results during or after review of X-ray films, and documentation of CAD results in electronic form.

In a further embodiment, the digitized label can be used to automatically group digitized X-ray films belonging to the same patient. This can be achieved by digitally comparing the labels of different films using image comparison techniques and using pre-determined correlation criteria to relate the films.

In yet a further embodiment, sub-labels can be digitally extracted from a label and associated with corresponding X-ray film images and or image analysis results such as CAD. By enabling the identification of images using selected information from the label, the method provides increase flexibility for retrieving desired films.

BRIEF DESCRIPTION OF THE DRAWINGS

Further features and advantages of the present invention will become apparent from the following detailed description, taken in combination with the appended drawing, in which.

DETAILED DESCRIPTION OF THE PREFERRED EMBODIMENT

Individual X-ray films are labeled with patient information that is "burned" into the film. This is accomplished with a device that exposes a small (approximately 1×2 inches) area of the film with alpha-numeric information that typically lists the patient name, birth date, identification number, accession number, and the name or identifier of the technologist;

Depending on the institution and the devices, the patient information area may be in the same place on all films, or it may vary. It may be on the edge of the film, or it may be somewhere in the background area outside of the anatomical feature shown on the film. It may have black on white text, or white on black text, it may be typed, or computer generated, and the fields and their alignment may differ from institution to institution, imaging device to imaging device, and exam to exam.

In one aspect of the present invention, the area of patient information (i.e. the label) can be used as the digital identifier of a patient, in lieu of any other digital identifier. Thus there is provided a method and system for identifying digitized X-ray films comprising a label which contains alpha-numeric information related to the patient and other information such as but not limited to conditions of exposure of the film.

Figure 1:
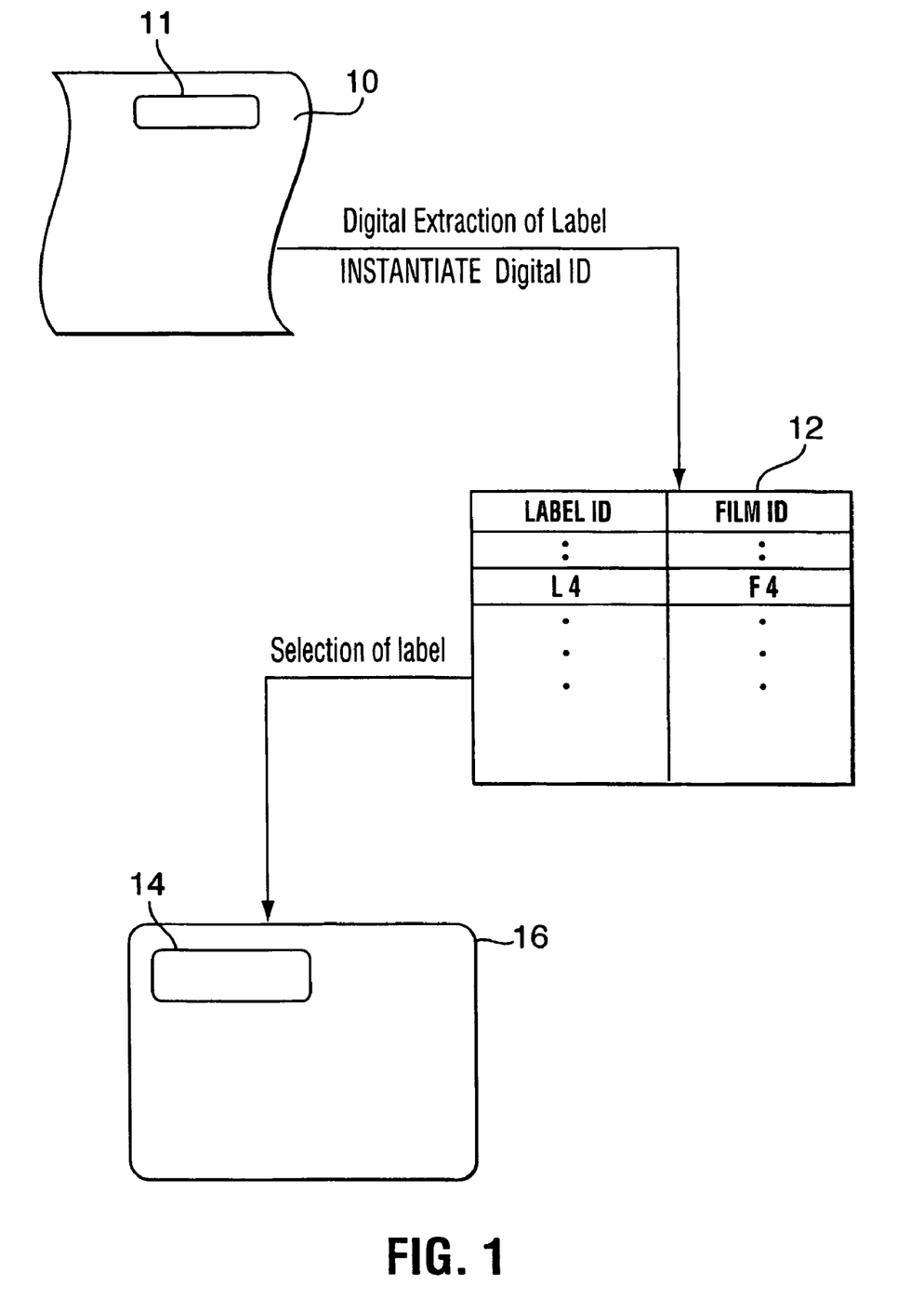
FIG. 1 is a schematic representation of the identification process using digitized X-ray film label according to an embodiment of the invention.

Referring to FIG. 1, a digitized image of the label 11 is obtained from X-ray film 10 and is digitally associated, in look-up table 12, with the corresponding digitized X-ray film. The digitized label 14 is displayed on a user interface 16 such as computer screen to allow the user to identify the corresponding film using the alpha-numeric information on the label. The image of the label can be displayed alone or simultaneously with the X-ray film image.

Figure 2:
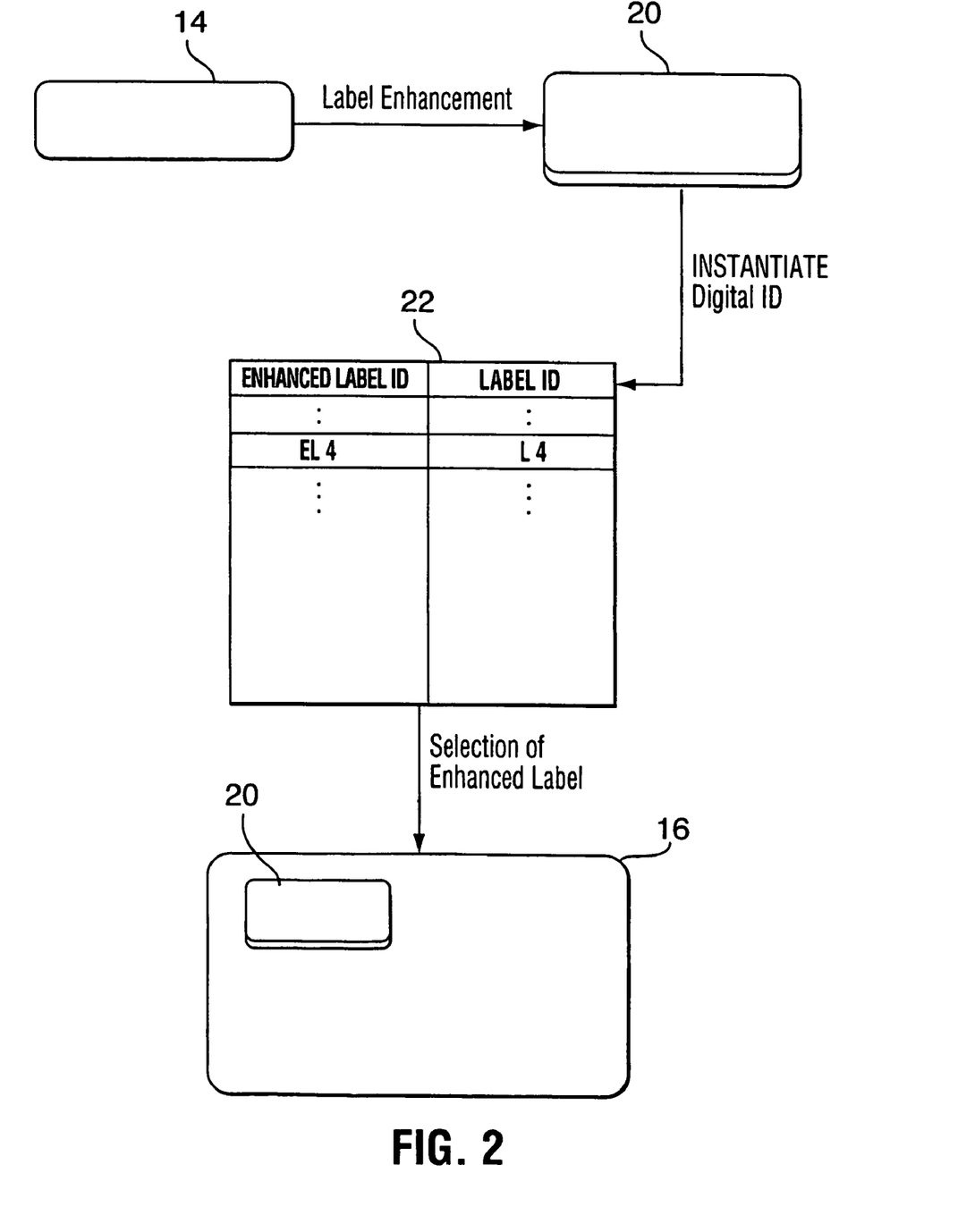
FIG. 2 is a schematic representation of the label enhancement process according to an embodiment of the invention.

In some cases the digitally extracted label may have textured background, be blurred or the contrast may not be important enough to allow easy reading of the information by the user. In these cases the label can be digitally enhanced. By label enhancement it is meant that certain procedures are performed to, for example, remove textured background, increase the contrast between the alpha-numeric characters and the background and enlarge the image. These procedures are well known in the art. Thus, and by referring to FIG. 2 the label 14 can be enhanced into an enhanced label (EL) 20 and digitally associated in look-up table 22 with either the corresponding X-ray film or the corresponding (non-enhanced) label or both. It will be appreciated that if the EL is associated with its corresponding label it can therefore be indirectly associated with the corresponding digitized X-ray film.

Figure 3:
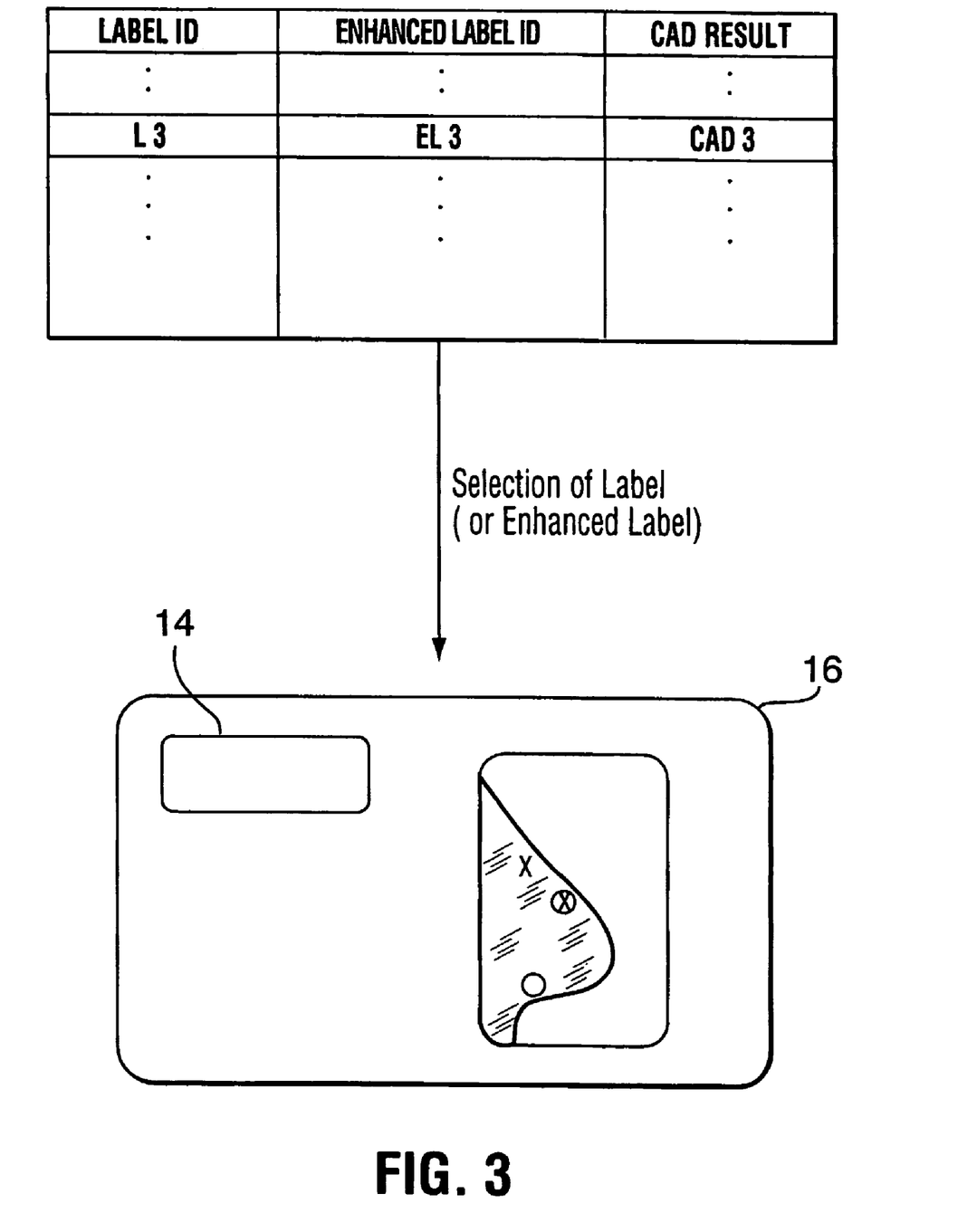
FIG. 3 is a schematic representation of the association and displaying of labels with CAD results according to an embodiment of the invention.

Image analysis algorithms such as CAD algorithms can be applied to the digitized films, and the results can be associated with the label (or EL) and corresponding X-ray film images (FIG. 3). The patient information area (label or EL) serves as the unique identifier of the patient, the images, and the image analysis results. Thus the label can be displayed simultaneously with the X-ray film image and the CAD results or, alternatively, the label can be displayed with the image analysis results alone.

In a preferred embodiment the digitized label is obtained by automatically locating and digitally extracting it from the remainder of the digitized X-ray film. To that effect, pattern recognition and image processing methods, which are known in the art, can be used. Such methods may include but are not limited to edge detection and texture segmentation. For example, in edge detection, the gradient of pixels intensity of an image is determined and used to identify a portion of the image wherein the gradient corresponds to a predetermined gradient, characteristic of the presence of the label. The extracted digital label will be used to identify the images of a case.

In another aspect of the invention, the user is presented with a user interface to interactively identify the location of the patient information area, and this area is then digitally extracted.

In yet another aspect of the invention, standard locations of the patient information area in films of different orientation are stored on the computer disk. Depending on the orientation of the film, the standard location of the patient information area on the film can be looked up, and the patient information area can be extracted from that area.

It should be noted that the extraction of the patient information area corresponds to selection of a sub-image in the digitized X-ray image, but not necessarily actual elimination of the remainder of the image (the complement of the sub-image). As is familiar to those skilled in the art, the extraction of a sub-image can be achieved both by copying the pixel elements of a sub-image into a new image buffer, and maintaining the sub-image as a separate image; or by identifying a rectangular region in the original image, and representing the new sub-image in the form of a reference to the original image and the co-ordinates of the rectangular region in that original image. The actual representation of the extracted area and sub-image is largely determined by software architecture and design of a particular implementation of the present invention.

Figure 4:
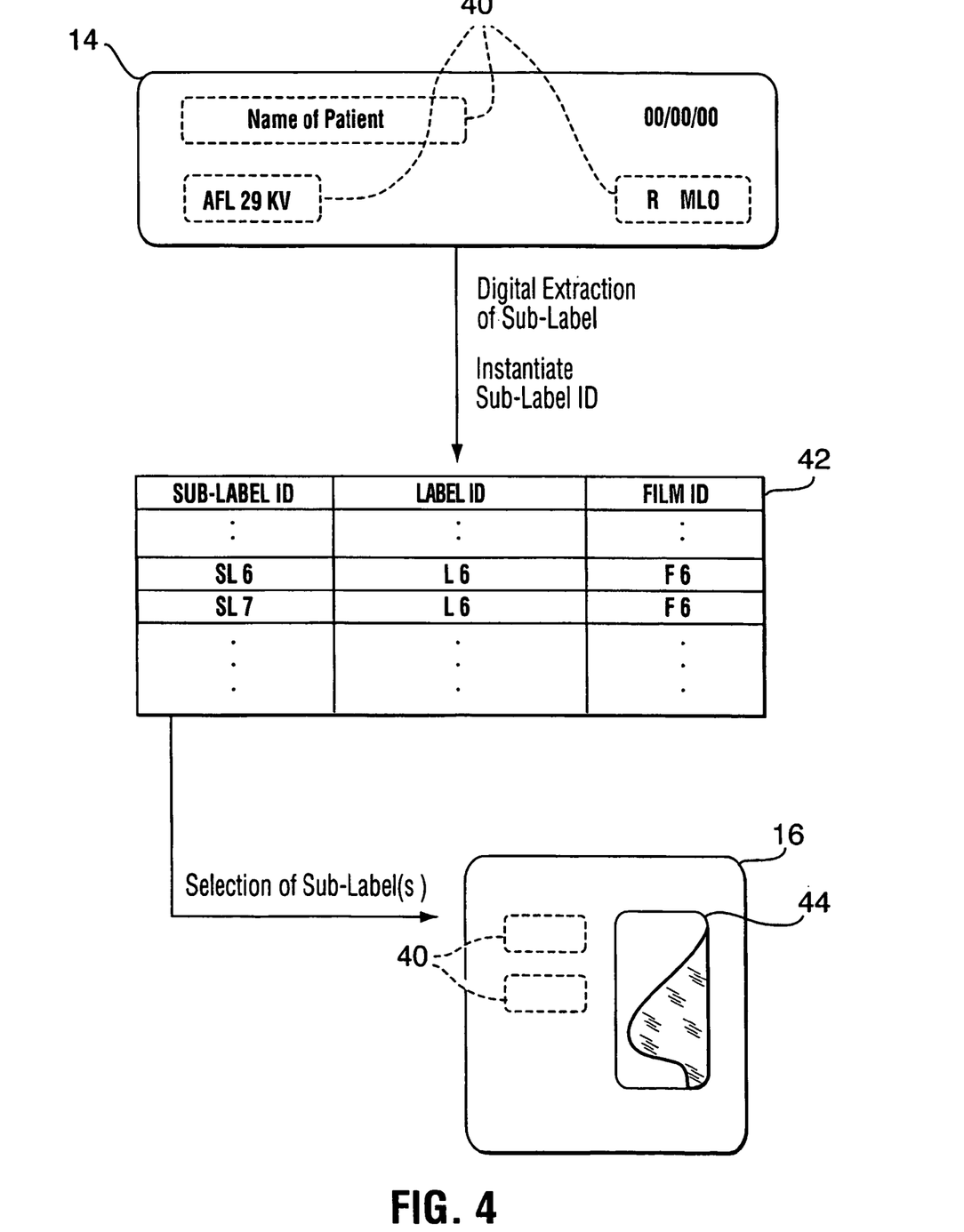
FIG. 4 is a schematic representation of the digital extraction and displaying of sub-labels according to art embodiment of the present invention.

In this respect, and referring to FIG. 4, the label 14 (or EL) may be subdivided into one or more sub-labels 40. As described above for the labels, the sub-labels can be digitally extracted and associated with the corresponding label, digitized X-ray film and/or image analysis results in a look-up table 42. Since more than one sub-label can be extracted from the label, different sub-labels may correspond to the same label of X-ray film image 44 or image analysis results. A sub-label may comprise the name of the patient or the voltage used during exposure of the film or orientation information (for example, medio-lateral-oblique (MLO) or cranio-caudal (CC)), and which side of the breast was imaged (Left or Right) or any other information contained in the label. It may also contain a combination or such information. The subdivision of the label advantageously allows the user to recall one or more film images based on information other than information that is exclusive to one patient such as the name of the patient.

A label detection application can be assigned to a digital image according to the method described in co-pending application U.S. Ser. No. 10/205,599 incorporated herein by reference. The method comprises the steps of: selecting a label acquisition model from a plurality of acquisition models based on at least one attribute of the digital label; and selecting a label detection application from a plurality of label detection applications using the selected label acquisition model.

In some embodiments, selection of an acquisition model may include the steps of: obtaining at least on one attribute of the digital label, and performing a search to identify the acquisition model using the obtained attributes. The label detection application may be selected by obtaining information concerning the digital label in accordance with the selected acquisition model and performing a search to identify the label detection application using at least the obtained information.

An example of a system that supports the assignment of a label detection application is also described in co-pending application U.S. Ser. No. 10/205,599 incorporated herein by reference. The system includes a case input system for selecting an acquisition model from a plurality of acquisition models, based on at least one attribute of the digital label, and for selecting a label detection application from a plurality of label detection applications using the selected acquisition model.

The system may further include an algorithm server for retrieving and applying the selected label detection application to the digital label.

It will be appreciated that other approaches car be used to assign a label detection application to a digitized X-ray film. For example the application could be a default application.

In diagnosis procedures, such as screening mammography, almost the same information is applied to all films of the same patient, although in many cases information pertaining to the individual film, such as X-ray current and orientation is also displayed on the label. Therefore, the labels may differ in some minor aspects.

Thus, all films for the same patient contain an area of about 1×2 inches that is very similar in content, but may be subject to variations in exposure, noise, and other artifacts. Hence the patient label extracted from one image of the case may be used to represent all images of the case, or all images of the patient. Thus in another aspect of the method of the present invention the images belonging to a patient can automatically be grouped using the digitized alpha-numeric information of the label. For grouping purposes, films of several patients are loaded into a digitizer, and the films are scanned and converted into digital form. No separator sheets are used, and films of several patients can be mixed. The area of patient information is automatically identified on each film, and correlated with the corresponding information on other films. Pairs of films with high correlation values for these patient information areas are considered to belong to the same patient, and pairs with low correlation values belong to different patients. Alternatively, character recognition can be performed on the identification area, and the patient name and other information is obtained directly in alpha-numerical form. This way, the patient name could be obtained and used as the identifier of a film, and films of each patient can be grouped based on the patient name.

Similarity between two films can be determined by comparing the patient information areas (labels) of the two films. Correlation methods, known to those skilled in the art, including but not limited to shift/rotation and intensity/contrast variations can be used to determine the similarity. A predetermined high correlation indicates that the two films belong to the same patient and a predetermined low correlation indicates that the two films belong to different patients.

Typically, films of consecutive patients are placed in the input tray of the digitizer. Films of one patient are grouped together, followed by the films of the next patient, etc. Therefore, the correlation method will be applied to pairs of consecutive films only. In most cases, there will be groups of four films, which exhibit a high correlation, and thus belong to one patient. Correlation between the last film of one patient and the first film of the next patient will be poor. Then, the four films of the next patient will exhibit high mutual correlation therefore enabling the grouping of the films that belong to the same patient.

Alternatively, it is also possible to scan films of multiple patients without grouping films of individual patients together. In that case, correlation is preferably performed between all pairs of individual film.

The digitized labels of each film on in a group can bet digitally associated with any or all digitized films belonging to this group. Therefore it is possible to display all the digitized film in a group by selecting only one label. It will be appreciated that any other display combination (1 label 2 films, 1 label 3 films 2 labels 3 films etc.) is possible within one group.

The method is not limited to groups of four films per patient. Any number of films per patient can be treated and identified with the correlation method.

Figure 5:
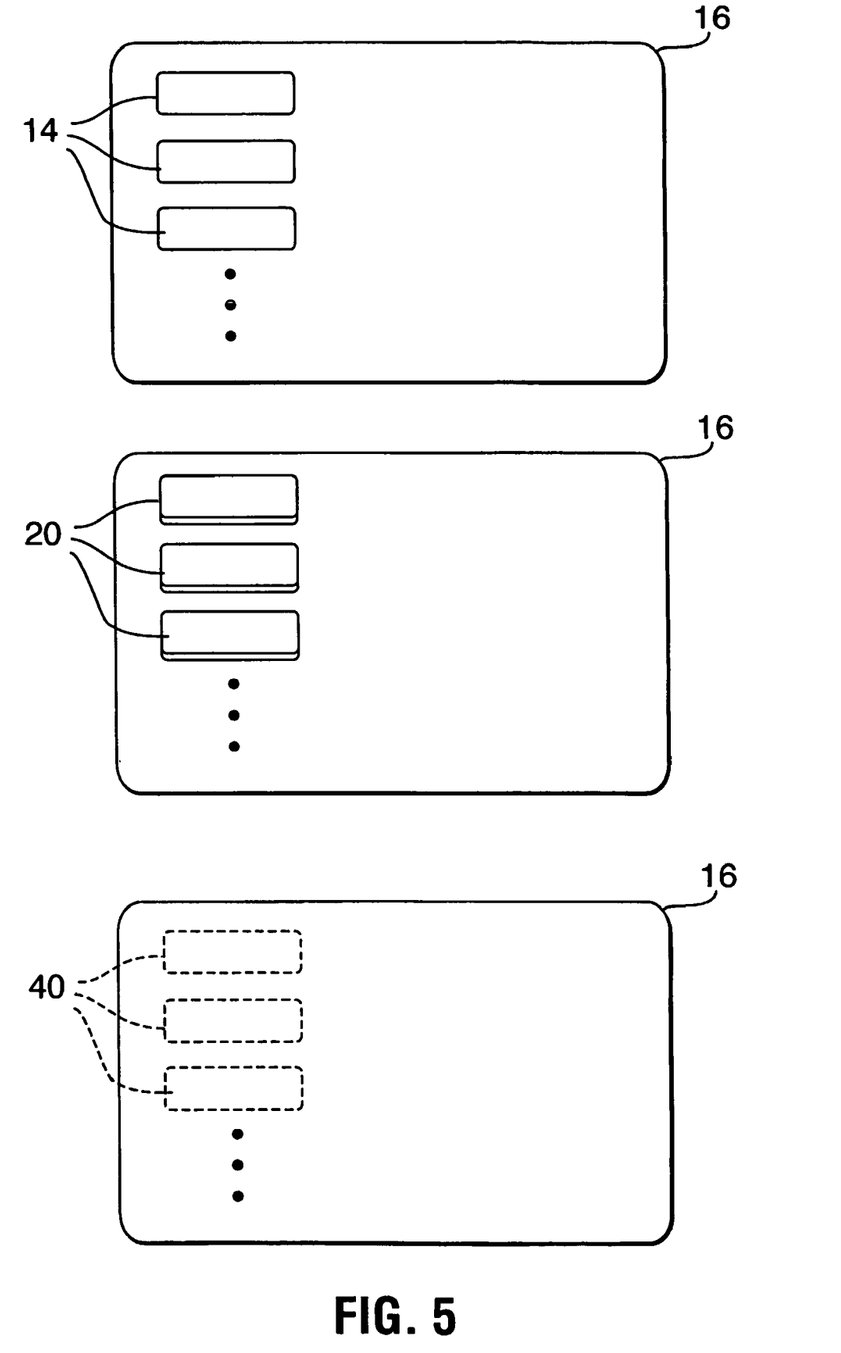
FIG. 5 is a schematic representation of the labels lists to select and retrieve corresponding X-ray film imagery according to an embodiment of the invention.

Using the method of the present invention, an X-ray film image can be selected and retrieved from a plurality of stored images. Now referring to FIG. 5, the labels (or EL or sub-labels) corresponding to all or a predetermined number of the stored films can be displayed on user interface to allow the user to select one or north desired X-ray film. It will be appreciated that image analysis results, such as CAD, can also be retrieved according to this embodiment. For example, the labels (or EL or sub-labels) of all available patients can be displayed on a computer monitor in a list. A technologist creates a "worklist" of CAD results (for example, corresponding to the order of x-ray films on an alternator or light box) through manipulation of digital patient identifiers (i.e. the labels) in a list displayed at the user interface. For example, this could be a scrollable list, and "cut-and-paste" within the list could be used to change the order. Or, two lists can be used, one for all available patients, and one for the worklist. The technologist can move the digital identifiers from one list to the other in the desired order using a mouse or a touch screen user interface for example. Displaying of the labels in a list also enables the user to directly select the name of one or several desired patients without the need to cross-refer the name of the patient with an ID number or to scan a bar code on a film.

Figure 6:
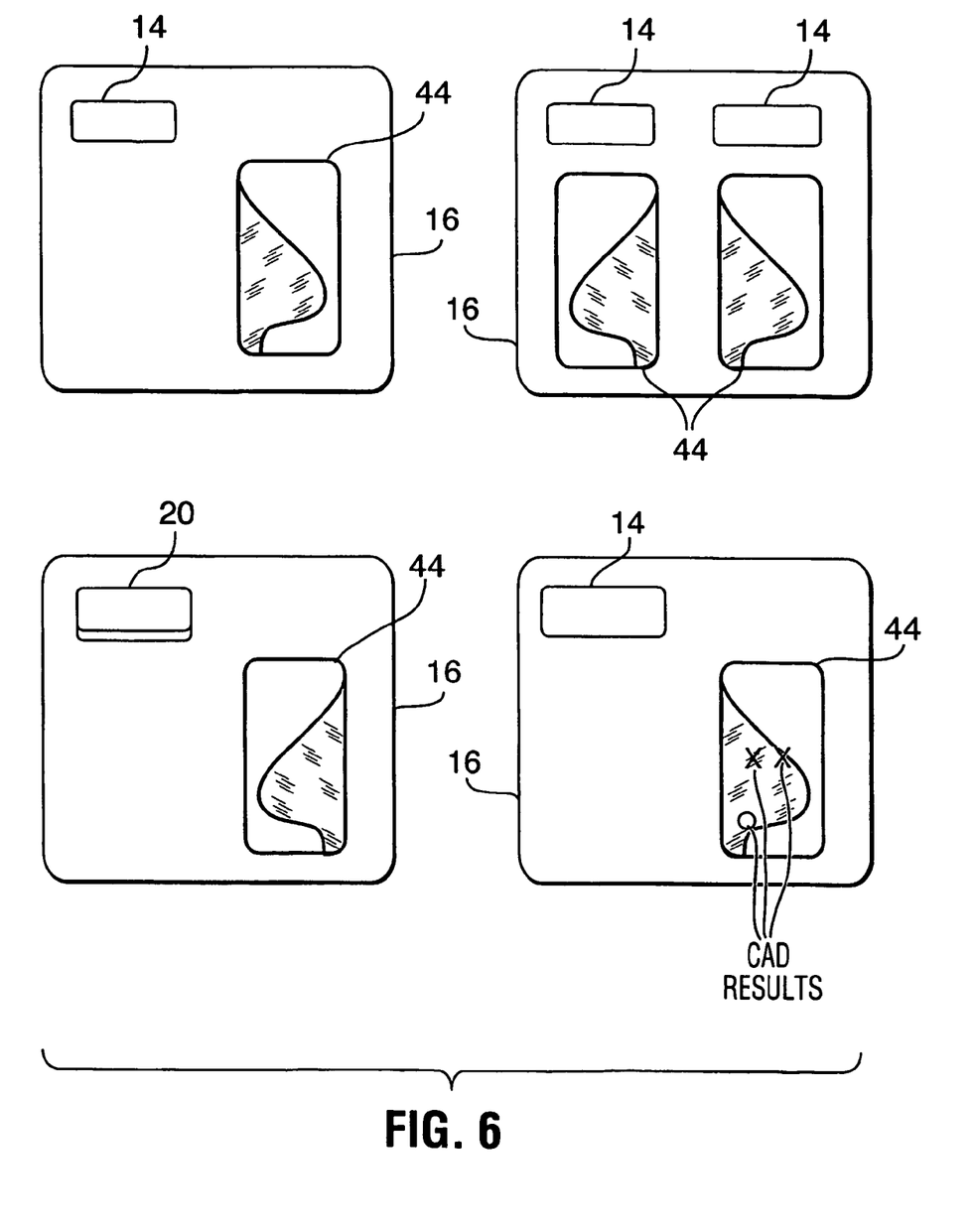
FIG. 6 is a schematic representation of label/film display combinations according to possible embodiments of the invention.

FIG. 6 shows possible embodiments of label/film displays wherein the label can be displayed simultaneously with the digitized film and/or with image analysis results. It will be appreciated that other display arrangements/combinations are possible.

Further, the digital labels could be used to arrange cases into a sequence, for example to create an ordered worklist of patients to be reviewed by a radiologist, as the films of the patient are hung on an alternator.

Also, the digital labels could be used to arrange that cases into a two-dimensional table, corresponding to the layout of the cases on a light box.

During the reading process, the CAD results are displayed on a monitor in proximity to the alternator or view box. In typical workflow, the CAD results are displayed after (for a "second read scenario") the radiologist has analyzed the images, to obtain prompts for additional suspicious areas. After review of the films, the radiologist selects the corresponding patient information area on the monitor (using a mouse, or a touch screen, for example). Next, the corresponding images and CAD results are displayed on the same monitor. This is possible because the images and CAD results are digitally associated with the patient information area.

The digitally extracted label can be used whenever the digital image is displayed on a monitor or printed on media. Furthermore, by visually associating the digital image with the digitally extracted label using graphics, tabular alignment, color coding, or any other such method, the user can recognize that the label and its associated image are indeed related, and will thus be able to identify the image as belonging to a particular patient.

It will be appreciated that the above described method of identifying X-ray images of a patient can be used on the digitization station, where images are displayed after digitization for quality control purposes or on a CA) results display station, which is used by radiologists to review areas that may have been deemed suspicious of disease by CAD.

In another aspect of the invention there is provided a system for identifying and retrieving digitized X-ray films having a label, the system comprises: an X-ray film digitizer for generating a digital image of each X-ray film; processor means for determining a position of the label on the digital image of the X-ray film; processor means for digitally extracting an image of the label from the digital image of the x-ray film; processor means for digitally associating the image of the label with the digitized image of the X-ray film; a screen for displaying the label. The system may also comprise a processor means for digitally associating the label with image analysis results of a corresponding digitized image of the X-ray film and processor means for analyzing the images of a plurality of labels.

The system may further comprise means for displaying images of one or more labels, user interface means for permitting a user to select one of the displayed labels, processor means for retrieving a digitized image of an X-ray film associated with the selected label and display means for displaying the retrieved digitized images of the X-ray films for examination by the user.

The embodiments of the invention described above are intended to be exemplary only. The scope of the invention is therefore intended to be limited solely by the scope of the appended claims.

The invention claimed is:

1. A method for retrieving, from a plurality of digitized x-ray films, a digitized x-ray film said film comprising at least one label, the method comprising the steps of:
    (i) obtaining a digital image of said label;
    (ii) digitally associating said digitized image of the label with said digitized x-ray film;
    (iii) displaying a plurality of labels each associated with a digitized x-ray film; and
    (iv) selecting a label from said plurality of labels to retrieve said digitized x-ray film.

2. The method as claimed in claim 1 further comprising the step of digitally associating the label with a corresponding image analysis result of the digitized x-ray film.

3. The method as claimed in claim 2 wherein said image analysis is a Computer Aided Detection (CAD) analysis.

4. The method as claimed in claim 1 wherein said step of obtaining a digital image of the label comprises:
    (i) determining position of said label on said film; and
    (ii) digitally extracting said image of said label.

5. The method as claimed in claim 4 wherein said step of determining is performed automatically.

6. The method as claimed in claim 5 wherein said step of determining position is performed using a method selected from edge detection and texture segmentation.

7. The method as claimed in claim 4 wherein said step of determining is performed by a user.

8. The method as claimed in claim 1 further comprising the step of displaying said x-ray film.

9. The method as claimed in claim 1 further comprising the step of digitally enhancing said image of the label prior to displaying said image of the label.

10. The method as claimed in claim 9 wherein said step of digitally enhancing comprises removing textured background and increasing contrast between background and alpha-numeric characters in said image of the label.

11. The method as claimed in claim 1 wherein image analysis results are associated with said digitized image and wherein the method further comprises the step of displaying corresponding image analysis results of the digitized x-ray film.

12. The method as claimed in claim 11 wherein said image analysis is CAD analysis.

13. A method for automatically grouping digitized x-ray films comprising at least one label and belonging to a same case and/or patient the method comprising the steps of:
(i) obtaining a digital image of said label;
(ii) digitally associating said digitized image of the label with said digitized x-ray film;
(iii) analyzing images of a plurality of labels associated with respective digitized x-ray films;
(iv) identifying labels within said plurality of labels having a desired degree of correlation sufficient to indicate that said identified labels belong to said same case and/or patient; and
(v) digitally grouping digitized x-ray films corresponding to said identified labels.

14. The method as claimed in claim 13 wherein said step or analyzing is performed using shift/rotation or intensity/contrast variations.

15. The method as claimed in claim 13 wherein each of said identified labels is associated with each film belonging to said same case and/or patient and wherein any one of said labels can be selected to effect display of all of said films.

16. The method as claimed in claim 13 wherein said label is one or more sub-label.

17. The method as claimed in claim 16 wherein said one or more sub-label comprises information selected from name of said patient, exposure voltage and orientation.

* * * * *